United States Patent [19]

Ginnaga et al.

[11] Patent Number: 4,996,299

[45] Date of Patent: Feb. 26, 1991

[54] METHOD FOR PREPARING PERTUSSIS TOXIN TOXOID USING HCHO AND AMINO ACIDS

[75] Inventors: Akihiro Ginnaga, Kumamoto; Kazunori Morokuma, Houtaku; Katsutoshi Aihara, Kamoto; Mitsuo Sakoh, Kumamoto, all of Japan

[73] Assignee: Juridical Foundation The Chemo-Sero-Therapeutic Research Institute, Kumamoto, Japan

[21] Appl. No.: 442,148

[22] Filed: Nov. 28, 1989

[30] Foreign Application Priority Data

Nov. 29, 1988 [JP] Japan ................................. 63-303767

[51] Int. Cl.$^5$ ........................ A61K 39/10; C12N 9/12; C07K 3/08; C07K 15/04
[52] U.S. Cl. ..................................... 530/409; 424/88; 424/92; 435/193; 435/194; 530/405; 530/406; 530/410; 530/415; 530/416; 530/825
[58] Field of Search ............... 530/405, 406, 409, 410, 530/415, 416, 825; 424/88, 92; 425/193, 194

[56] References Cited

U.S. PATENT DOCUMENTS

| | | | |
|---|---|---|---|
| 4,762,710 | 8/1988 | Sekura | 530/410 X |
| 4,784,589 | 11/1988 | Robinson et al. | 424/92 |
| 4,788,058 | 11/1988 | Parton et al. | 424/92 |
| 4,845,036 | 7/1989 | Burns et al. | 435/194 |
| 4,849,358 | 7/1989 | Chazono et al. | 424/92 |
| 4,885,359 | 12/1989 | Ginnaga et al. | 424/92 |

FOREIGN PATENT DOCUMENTS 0121249  10/1984  European Pat. Off. .

OTHER PUBLICATIONS

Journal of Bacteriology in Japan, 42, 288, (1987), Sato et al.

*Primary Examiner*—Howard E. Schain
*Attorney, Agent, or Firm*—Fleit, Jacobson, Cohn, Price, Holman & Stern

[57] ABSTRACT

Disclosed is a method for preparing pertussis toxin toxoid by a treatment of pertussis toxin with formaldehyde, which comprises carrying out said treatment in the presence of lysine or glycine in combination with N-acetyltriptophan. The resultant toxoid does not exhibit toxicity reversion, thereby making the toxoid highly suitable for use in pertussis vaccines.

6 Claims, No Drawings

METHOD FOR PREPARING PERTUSSIS TOXIN TOXOID USING HCHO AND AMINO ACIDS

FIELD OF THE INVENTION

The present invention relates to a method for toxoidizing pertussis toxin, more particularly, to a novel method for preparing pertussis toxin toxoid from pertussis toxin by which the toxoid will not exhibit toxicity reversion, thereby making the toxoid highly suitable for use in pertussis vaccines having no substantial side effects.

PRIOR ART

Pertussis toxin is a protein produced by *Bordetella pertussis* and, because of the variety of its physiological and biological activities, is also referred to as leukocytosis promoting factor (LPF), histamine sensitizing factor (HSF), or islets activating protein (IAP). In addition, pertussis toxin is known to exhibit such biological activities as promotion of vascular permeability, CHO-cell clustering activity, and ADP-ribosylase activity.

It is also known that pertussis toxin is one of the most important antigens against infection with pertussis. Thus, attempts have been made to develop various pertussis vaccines indispensably containing pertussis toxin toxoid by treating pertussis toxin so as to destroy its toxicity while retaining its immunogenicity.

In treating pertussis toxin for obtaining the toxoid thereof, formaldehyde and glutaraldehyde have been most commonly used. However, it has recently been pointed out that treatment with formaldehyde and/or glutaraldehyde does not sufficiently inactivate the pertussis toxin and thus does not provide the toxoid which is totally devoid of all of the toxic physiological and biological activities. For example, Sato et al. have shown that the use of formaldehyde or glutaraldehyde for producing the toxoid from the pertussis toxin only decreases to a limited extent such properties as ADP-ribosylase activity and islets activating property, while substantially decreasing such properties as leukocytosis promoting activity, histamine sensitizing activity and hemagglutionation activity [Journal of Bacteriology in Japan, 42, 288(1987)]. Furthermore, it has recently been concerned that pertussis toxin toxoid obtained through the detoxification with the conventional agents such as formaldehyde may exhibit toxicity reversion during storage, thereby giving the vaccines containing the toxoid undesirable side effects (Pertussis Vaccine Workshop '87). It is therefore being recommended that the toxoid used be one having no substantial toxicity reversion, which may be determined, for example, by maintaining the toxoid at 37° C. for a period of several weeks.

It is therefore a primary object of the present invention to overcome the above-mentioned problems and to provide a novel method for preparing pertussis toxin toxoid from pertussis toxin by which the resultant toxoid is completely devoid of toxicity and does not exhibit toxicity reversion while retaining the sufficient antigenicity.

The above and other objects and features of the present invention will be apparent from the following description.

DESCRIPTION OF THE INVENTION

Through extensive studies, the present inventors have found that, in the treatment of pertussis toxin with formaldehyde (formalin) for the preparation of the toxoid, the presence of specific amino acids provide sufficient inactivation of the toxin without possibility of the toxicity reversion.

Thus, according to the present invention there is provided a method for preparing pertussis toxin toxoid by a treatment of pertussis toxin with formaldehyde, which comprises carrying out said treatment in the presence of lysine or glycine in combination with one or more of amino acids selected from the group consisting of N-acetyl-DL-triptophan, N-acetyl-D-triptophan and N-acetyl-L-triptophan.

The present inventors previously suggested that the presence of amino acid(s) may be advantageous in detoxification of antigens which are regarded as having preventive effect against the infection with pertussis (Japanese Patent Application No. 58548/1983). However, in the earlier application no mention was made specifically regarding the combination of lysine with N-acetyltriptophan (N-acetyl-DL-triptophan, N-acetyl-D-triptophan or N-acetyl-L-triptophan), or the combination of glycine with N-acetyltriptophan.

The present invention is based on the fact that the treatment of pertussis toxin with formaldehyde in the presence of N-acetyltriptophan together with lysine or glycine can produce toxoids which are much superior to those obtained by conventional detoxification methods including the ones described in the above-mentioned earlier application by the present inventors (Japanese Patent Appln No. 58548/1983) in which there are employed other amino acid(s) than those defined in the present invention. It is particularly notable that the pertussis toxin toxoid prepared by the method of the present invention does not exhibit substantial toxicity reversion even under severe conditions, as evidenced by an assay system recently developed for sensitive analysis.

The method of the present invention for the preparation of the toxoid is generally carried out with 0.2 to 1.2% of formalin for 5 to 50μg of pertussis toxin in terms of PN(protein nitrogen)/ml, in which the concentration of N-acetyltriptophan is in the range of 0.1 to 10mM, the concentration of lysine is in the range of 5 to 200mM and the concentration of glycine is in the range of 5 to 200mM, at a temperature of 20 to 45° C. for a treatment period of 3 to 30 days. Between lysine and glycine, lysine is preferable. The method of the present invention is practiced preferably with the formalin concentration being 0.3 to 1.0% (most preferably 0.6 to 0.8%), N-acetyltriptophan concentration being 0.2 to 4 mM (most preferably 0.5 to 2 mM), lysine concentration being 20 to 100 mM (most preferably, 10 to 50 mM), glycine concentration being 5 to 120 mM (most preferably 20 to 40 mM), and the temperature being 25 to 45° C. (most preferably 37 to 42° C. ) for a period of 7 to 21 days (most preferably 7 to 10 days).

In the toxoid prepared by the method of the present invention, the various physiological and biological activities possessed by the pertussis toxin are reliably inactivated for detoxification, while the immunogenicity is retained as can be confirmed by the mouse potency test. What is more, the pertussis toxin toxoid obtained by the present invention does not demonstrate substantial change in the degrees of the physiological and biological activities and does not produce toxicity reversion, even when maintained at 37° C. for a period of several weeks. Accordingly, the method of the present invention for the preparation of the toxoid is of outstanding utility for providing efficacious and safe pertussis vaccines.

The present invention will be more specifically described with reference to the following working example, which does not limit the scope of the present invention.

EXAMPLE

Pertussis toxin, 20 μg PN/ml (PN:protein nitrogen), was added with amino acid(s) as given in the table below. The mixture was added with formalin in an amount of 0.6 to 0.8% and the resultant was then kept at 40° C. for 7 to 21 days. After dialysis against PBS (M/75) to remove the formalin, pertussis toxin toxoids were obtained. Toxoid samples, 2μg PN/ml, were each added with aluminum gel, 0.2 mg/ml, to prepare vaccine solutions. Each vaccine solution was kept 4° C. for 4 weeks, or at 37° C. for 4 weeks. The vaccine solutions were then determined for the various physiological and biological activities, with the results as shown in the table.

Determinations of the physiological and biological activities were conducted in known ways described in the literature references given below:
Mouse Potency[MP]: Minimum Requirements of Biological Products in Japan 1981, edited by Ministry of Health of Japan
LPF activity (mouse LPF activity)[LPF]: ditto
HSF activity (mouse HSF activity)[HSF]: ditto
CHO-cell clustering activity (Chinese hamster ovary cell clustering activity)[CHO]: J. Biol. Stand., 13, 61–66(1985).
Skin vascular permeability [SVP]: Microbiol. Immunol., 31, 531–539(1987).
Blood glucose value [BGV]: Infect. Immun., 41, 137–144 (1983).
ADP-ribosylase activity (ADP-ribosyltransferase activity) [ADP]: Infect. Immun., 46, 422–428 (1984).

The toxoids (Sample Nos. 1,2,8 and 9) prepared according to the method of the present invention exhibited no toxic activities while possessing high potencies, as can been seen from the data on the physiological and biological activities given in the table. Particularly notable is that the toxoids obtained by the present invention demonstrated no toxic activities and no toxicity reversion even when maintained at 37° C. for four weeks. Such effect is particularly notable when N-acetyltriptophan and lysine are added.

In contrast, samples subjected to a single addition of N-acetyltriptophan, lysine or glycine (Samples Nos. 3,4 or 5) showed a tendency toward toxicity reversion as such toxoid samples still exhibited some extent of physiological and biological activities when maintained at 37° C. It will also be noted that the treatment with formalin alone (Sample No.6), as commonly practiced, does not provide satisfactory inactivation of the physiological and biological activities. This is particularly the case when the sample was maintained 37° C., since the results show that the substantial levels of the physiological and biological activities for toxicity are still remained.

| Sample No. | Amino Acid(s) | Condition | | | | Physiological and Biological Activities of Toxoids | | | | | |
|---|---|---|---|---|---|---|---|---|---|---|---|
| | | Amino Acid Con (mM) | Temp. (°C.) | Formalin Con. (%) | Period (days) | LPF | | HSF | | CHO | |
| | | | | | | 4° C. | 37° C. | 4° C. | 37° C. | 4° C. | 37° C. |
| 1 | N-acetyl-DL-triptophan lysine | 1.722 50 | 40 | 0.8 | 7 | 0.35 | 0.35 | 0.06 | 0.05 | <0.25 | <0.25 |
| 2 | glycine | 1.722 44 | 40 | 0.8 | 7 | 0.35 | 0.35 | 0.06 | 0.05 | <0.25 | 2.2 |
| 3 | (control) | 1.722 | 40 | 0.8 | 7 | 0.37 | 0.50 | 0.10 | 1.20 | <0.25 | 135 |
| 4 | (control) | 50 | 40 | 0.8 | 7 | 0.42 | 0.50 | 0.06 | 0.60 | <0.25 | 50 |
| 5 | (control) | 44 | 40 | 0.8 | 7 | 0.38 | 0.50 | 0.06 | 0.75 | <0.25 | 50 |
| 6 | No amino acid | 0 | 40 | 0.8 | 7 | 0.35 | 0.85 | 0.09 | 1.50 | 2.3 | 270 |
| (7) | Saline (for Biol. Activity Control) | 0 | 0 | 0 | 0 | 0.37 | 0.37 | 0.06 | 0.06 | <0.25 | <0.25 |
| 8 | | 0.574 10 | 40 | 0.8 | 14 | 0.35 | 0.35 | 0.06 | 0.06 | <0.25 | <0.25 |
| 9 | | 0.574 20 | 25 | 0.6 | 27 | 0.35 | 0.35 | 0.06 | 0.05 | <0.25 | <0.25. |

| Sample No. | Physiological and Biological Activities of Toxoids | | | | | |
|---|---|---|---|---|---|---|
| | SVD | | BGV | | ADP | MP |
| | 4° C. | 37° C. | 4° C. | 37° C. | 4° C. | (IPU/ml) |
| 1 | — | — | 220 | 215 | — | 13.1 |
| 2 | — | — | 215 | 190 | — | 14.0 |
| 3 | — | — | ND | ND | — | 11.0 |
| 4 | — | — | ND | ND | — | 8.0 |
| 5 | — | — | ND | ND | — | 11.5 |
| 6 | + | + | 189 | 185 | + | 12.2 |
| (7) | — | — | 217 | 210 | — | 0 |
| 8 | — | — | 220 | 217 | — | 12.5 |
| 9 | — | — | 210 | 215 | — | 12.7 |

ND: No experiment was done.

What is claimed is:

1. A method for preparing pertussis toxin toxoid by a treatment of pertussis toxin with formaldehyde, which comprises carrying out said treatment in the presence of lysine or glycine in combination with one or more of amino acids selected from the group consisting of N-acetyl-DL-triptophan, N-acetyl-D-triptophan and N-acetyl-L-triptophan.

2. The method as claimed in claim 1, in which 0.2 to 1.2% of formalin is used for 5 to 50g of pertussis toxin in terms of PN(protein nitrogen)/ml, the concentration of N-acetyltriptophan is in the range of 0.1 to 10 mM, the concentration of lysine is in the range of 5 to 200 mM and the concentration of glycine is in the range of 5 to 200 mM, at a temperature of 20 to 45° C. for a treatment period of 3 to 30 days.

3. The Method as claimed in claim 2, in which the formalin concentration is 0.3 to 1.0%, N-acetyltriptophan concentration is 0.5 to 2 mM, lysine concentration is 10 to 50 mM, glycine concentration is 20 to 40 mM, and the temperature is 37 to 42° C. for a period of 7 to 10 days.

4. The method as claimed in any of claims 1 through 3, in which lysine is used.

5. The method as claimed in claim 2 in which lysine is used.

6. The method as claimed in claim 3 in which lysine is used.

* * * * *